United States Patent [19]

Zarate

[11] Patent Number: 5,662,619

[45] Date of Patent: Sep. 2, 1997

[54] VENOUS DIALYSIS NEEDLE

[76] Inventor: Alfredo R. Zarate, 8128 Hamilton Springs Rd., Bethesda, Md. 20817

[21] Appl. No.: 563,210

[22] Filed: Nov. 27, 1995

[51] Int. Cl.$^6$ .............................. A61M 5/32; A61M 5/00; A61M 25/00

[52] U.S. Cl. .............................. 604/272; 604/264; 604/246

[58] Field of Search .......................... 604/239, 264, 604/272, 158, 161, 164, 169, 170, 171, 22, 27, 29, 30, 48, 93, 131, 246–247, 256, 4–6; 606/108, 167, 170, 184, 185

[56] References Cited

U.S. PATENT DOCUMENTS

| | | |
|---|---|---|
| 1,273,542 | 7/1918 | Schooler . |
| 2,748,769 | 6/1956 | Huber et al. . |
| 3,492,992 | 2/1970 | Kurtz . |
| 3,603,311 | 9/1971 | Huggins ............................ 604/161 |
| 4,134,402 | 1/1979 | Mahurkar ........................... 604/44 |
| 4,180,068 | 12/1979 | Jacobsen et al. . |
| 4,236,520 | 12/1980 | Anderson ........................... 128/348 |
| 4,411,657 | 10/1983 | Galindo ............................. 604/274 |
| 4,431,426 | 2/1984 | Groshong et al. ................... 604/280 |
| 4,643,712 | 2/1987 | Kulik et al. ........................ 604/4 |
| 4,675,004 | 6/1987 | Hadford et al. ..................... 604/44 |
| 4,838,877 | 6/1989 | Massau ............................. 604/272 |
| 4,968,306 | 11/1990 | Huss et al. ........................ 604/264 |
| 4,968,307 | 11/1990 | Dake et al. ....................... 604/264 |
| 4,993,941 | 2/1991 | Maita et al. . |
| 5,100,395 | 3/1992 | Rosenberg .......................... 604/247 |
| 5,180,364 | 1/1993 | Ginsburg ........................... 604/247 |
| 5,224,938 | 7/1993 | Fenton, Jr. ........................ 604/247 |
| 5,254,106 | 10/1993 | Feaster ............................ 604/272 |
| 5,330,433 | 7/1994 | Fonger et al. ..................... 604/164 |
| 5,360,416 | 11/1994 | Ausherman et al. ................. 604/272 |
| 5,484,417 | 1/1996 | Waitz et al. ...................... 604/239 |

OTHER PUBLICATIONS

Webster's II New Riverside University Dictionary, Houghton Mifflin Company, 1994, pp. 169, 185.

*Primary Examiner*—Corrine M. McDermott
*Assistant Examiner*—Bhisma Mehta
*Attorney, Agent, or Firm*—Foley & Lardner

[57] ABSTRACT

A dialysis needle using lateral openings and diverters. The diverters increase the blood flow through the lateral openings in venous needles.

11 Claims, 3 Drawing Sheets

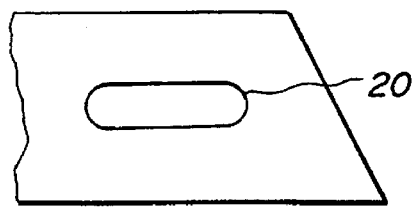
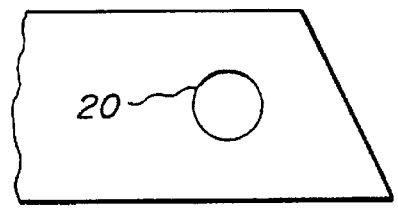
FIG. 6
FIG. 7
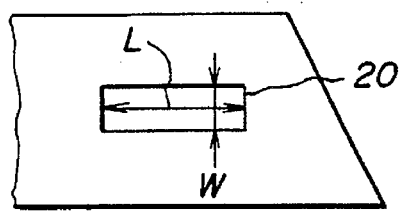
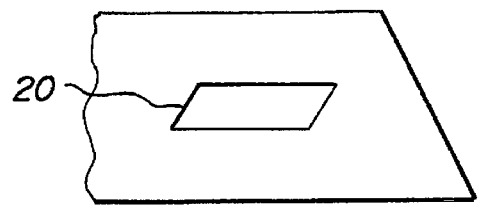
FIG. 5
FIG. 8
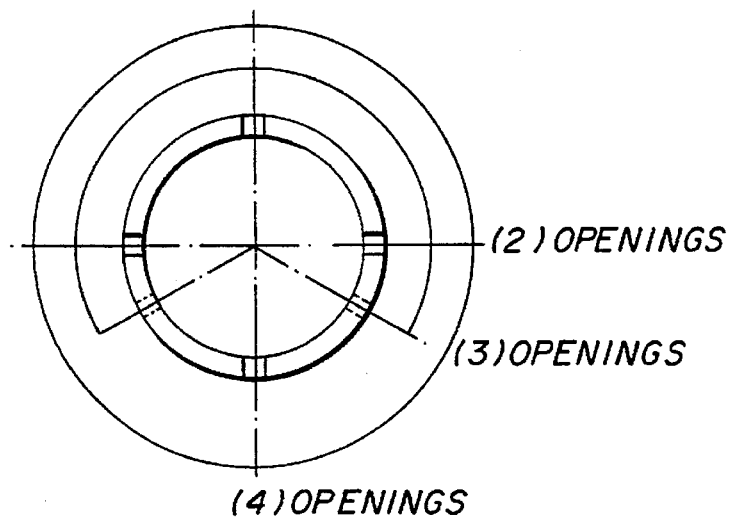
FIG. 9
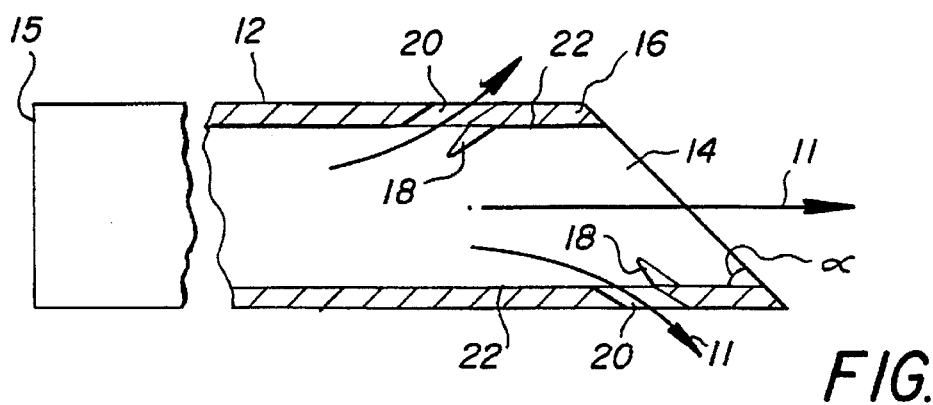
FIG. 10

VENOUS DIALYSIS NEEDLE

FIELD OF THE INVENTION

The invention relates generally to the field of dialysis needles. The invention involves particularly the use of multiple holes in the distal end of a venous needle with diverters on its interior surface. The diverters serve to divert blood from a distal opening to lateral openings and thereby slow the flow of blood. This invention also involves using a similar needle as an arterial needle, which will decrease the suction and related tearing of the intima and recirculation of blood through the dialyzer.

BACKGROUND OF THE INVENTION

During the past thirty years, since the beginning of two-needle dialysis, many advances in dialysis technology have occurred. Since dialysis with two needles was begun, the dialyzer has increased in efficiency. The volume of blood delivered to the dialyzer to be processed per minute has increased from 200 cc/m to 400–600 cc/m. While this increase in efficiency reduces the amount of time dialysis takes, needle technology has not kept up with the overall level of dialysis technology.

Since needle technology has remained virtually unchanged in this field, the increased volume of blood causes an exponential increase of the positive pressure and velocity of the jet of blood exiting the venous needle. Using slightly larger needles has decreased the pressure and velocity of the blood jet to a certain extent. However, the use of larger needles is problematic since larger needles cause greater damage to a patient's skin and blood vessels.

Thus, it is necessary to design a new venous dialysis needle which will decrease the velocity, turbulence and shear stress the increased flow of blood causes.

Accordingly, one object of this invention is to decrease the velocity and pressure of the jet of blood exiting the needle's distal opening in order to decrease the shear stress on the endothelium inside the graft and in the venous anastomosis when operating in a dialysis set up to process 400–600 cc/m.

Another object of the invention is to decrease the turbulence of the blood reaching the venous anastomosis during dialysis.

Yet another object of the invention is to allow the use of needles of smaller diameter to decrease the trauma to the endothelium, graft, and skin.

Yet another object of the invention is to decrease the negative pressure of blood entering the arterial needle, reducing the risk of tearing the intima.

Yet another object of the invention is to decrease the risk of recirculation of previously processed blood from the venous needle back through the arterial needle and dialyzer.

SUMMARY OF THE INVENTION

A preferred embodiment of the invention which is intended to accomplish at least some of the foregoing objects includes a dialysis needle having a hollow shaft. The hollow shaft has an exterior surface, an interior surface, a central axis, an open proximal end, an open distal end, and at least two lateral openings. The dialysis needle also includes a diverter located on the interior surface of the shaft adjacent each of the lateral openings. Each diverter is fixed in position and projects into the lumen of the shaft at an angle toward the central axis of the shaft.

BRIEF DESCRIPTION OF THE DRAWINGS

FIG. 5 is a side view of the needle showing the structure of the lateral openings in the preferred embodiment;

FIG. 6 is a side view of the needle showing the structure of a first alternative embodiment of the lateral openings;

FIG. 7 is a side view of the needle showing the structure of a second alternative embodiment of the lateral openings;

FIG. 8 is a side view of the needle showing the structure of a third alternative embodiment of the lateral openings;

FIG. 9 is a schematic showing the locations of the lateral openings on the needle;

FIG. 10 is a schematic drawing showing the general direction of blood flow from the needle in the preferred embodiment;

DESCRIPTION OF THE PREFERRED

Figure 1:
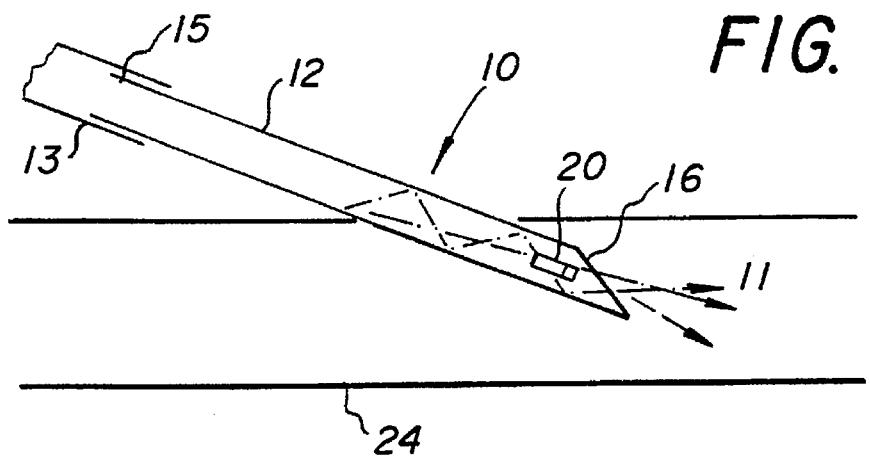
FIG. 1 is a schematic of the needle of the present invention in use during dialysis.

Referring to the drawings, FIGS. 1 and 10 show the preferred embodiment of dialysis needle, marked generally as 10. Blood 11 flows from tubing 13 into proximal opening 15 and down hollow shaft 12 of dialysis needle 10. A portion of blood 11 flows out distal opening 14 in distal end 16. Another portion of blood 11 impinges on diverters 18 and flows out lateral openings 20. Distal end 16 is bevelled at an angle alpha of between 25 and 35 degrees to assist in easy penetration of blood vessel 24. Shaft 12 is straight. However, in an alternative embodiment of the invention (not shown), shaft 12 may be bent.

Diverters 18 are on interior surface 22 of shaft 12. There is at least one lateral opening 20 in and one diverter 18 on shaft 12. Each diverter 18 is between lateral opening 20 and distal end 16. Diverters 18 protrude about 0.1 mm into shaft 12.

It will be clear to one of ordinary skill in the art that blood may be diverted through lateral openings 20 through various diverters. Three embodiments are currently contemplated, but these embodiments are described only for example and other embodiments may be constructed while coming within the scope of the invention.

Figure 2:
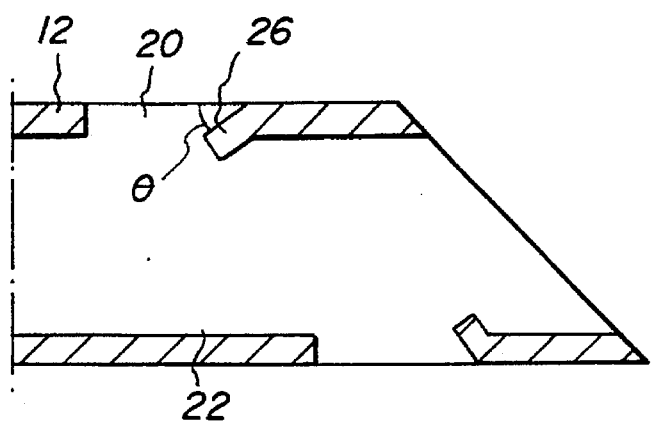
FIG. 2 is a cross-section of the needle of the present invention showing the diverters used in the preferred embodiment.
Figure 3:
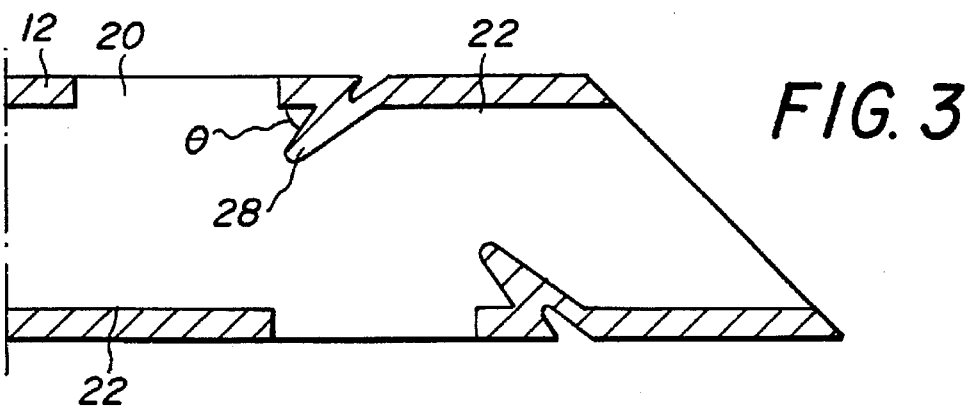
FIG. 3 is a cross-section of the needle of the present invention showing a first alternative embodiment of the diverters.
Figure 4:
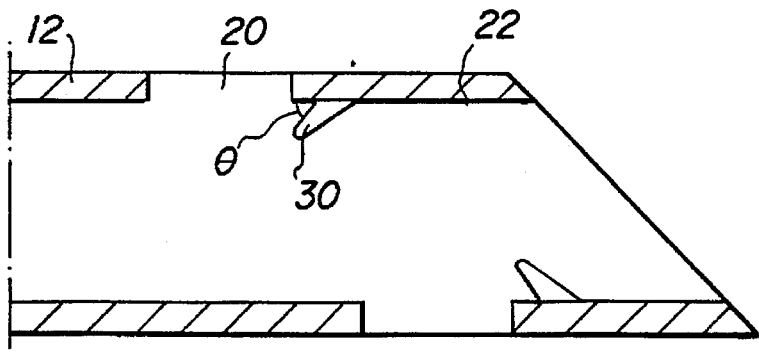
FIG. 4 is a cross-section of the needle of the present invention showing a second alternative embodiment of the diverters.

Referring to FIGS. 2–4, a variety of diverters may be seen. The preferred embodiment is shown in FIG. 2, where diverter 26 on interior surface 22 is formed by bending a piece of shaft 12 inwardly to an angle theta of between 5 and 45 degrees. In a first alternative embodiment shown in FIG. 3, diverter 28 on interior surface 22 is formed by making an indentation in shaft 12, most preferably with a pointed object. The shaft is indented at angle theta. In a second alternative embodiment shown in FIG. 4, diverter 30 on interior surface 22 is ether integrally formed with shaft 12 or a material is later added to the interior surface of shaft 12 to form a diverter. The diverter is again at angle theta.

As shown in FIG. 5, the preferred embodiment of lateral opening 20 is rectangular. However, it will be clear to one of ordinary skill in the art that lateral openings 20 may take a variety of shapes. Three alternatives to the rectangular shape of the preferred embodiment are currently contemplated, but these embodiments are described only for example and other embodiments may be constructed while coming within the scope of the invention.

As shown in FIG. 6, a first alternative embodiment is an oval lateral opening 20. FIG. 7 shows circular lateral opening 20. FIG. 8 shows lateral opening 20 in a parallelogram shape.

In order to reduce the risk of extravasation, limitations on the sizes of lateral openings 20 and the distance between lateral openings 20 and distal end 16 are important. Lateral opening 20 is between about 0.8 mm and 2mm from distal end 16. The invention is intended to be used in 14 g, 15 g, and 16 g needles. Lateral openings 20 should be about 1.2 mm in width (W) by about 1.5 mm in length (L), as shown in FIG. 5.

In addition to the varying sizes, the dimensions of lateral openings 20 may be varied depending on the size of the needle.

When a larger needle (14g) is used, the dimensions of the lateral openings may increase to about 1.4 mm in width and 1.6 mm in length. In no case should the lateral openings be longer than 1.6 mm to minimize the risk of extravasation.

The number of lateral openings is variable. While the preferred embodiment has two lateral openings 20, the person of ordinary skill in the art will recognize that a larger or smaller number of lateral openings 20 may be used. Regardless of the number of lateral openings 20, lateral openings 20 should be approximately evenly spaced around the circumference of shaft 12. The locations are illustrated in FIG. 9. Using more than four lateral openings 20 or more than one row of lateral openings 20, while possible, may not be advisable depending on the size of each lateral opening, because a larger number of lateral openings 20 will tend to weaken distal end 16 of shaft 12.

Figure 11:
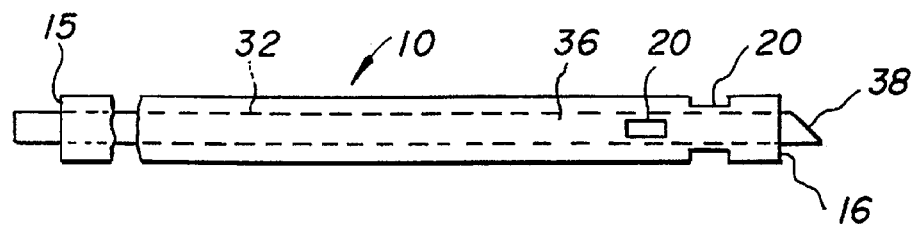
FIG. 11 is a schematic of a first alternative embodiment of the needle.
Figure 11A:
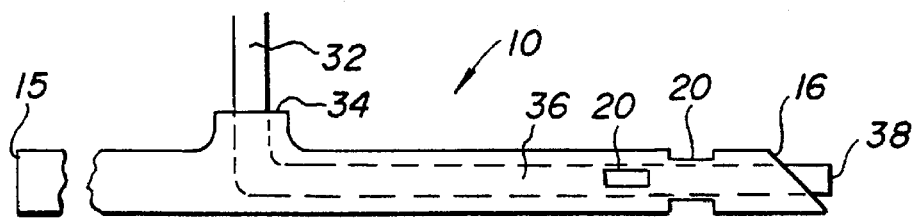
FIG. 11a is a schematic of an alternative embodiment of the first alternative embodiment of the needle.

If it is desired to use a larger number of lateral openings, it is advisable to use the needle 10 with a trocar 32 as shown in a first alternative embodiment in FIGS. 11 and 11a. When needle 10 is used with trocar 32 and two rows of lateral openings 20, the rows should be offset as shown so as to not greatly weaken distal end 16. Trocar 32 has a shaft 36 and a distal end 38. As shown in the first alternative embodiment in FIG. 11a, distal end 38 of trocar 32 is blunt while distal end 16 of needle 10 is bevelled. In an alternative to the first alternative embodiment shown in FIG. 11, distal end 16 of needle 10 is blunt while distal end 38 of trocar 32 is bevelled. It will also be obvious to one of ordinary skill in the art that the distal end 16 of needle 10 and the distal end 38 of trocar 32 may both be bevelled. However, the combination should not be used when the distal end 16 of needle 10 and the distal end 38 of trocar 32 are both blunt, as there is a greater danger of damaging the skin or intima when no bevel is used. Trocar 32 must be removed after insertion into the patient but prior to use of needle 10 in dialysis. Trocar 32 may be removed from shaft 12 through proximal opening 15 or through additional opening 34. Although the additional opening 34 is shown only in FIG. 11, it will be obvious to one of ordinary skill in the art that either method of removing trocar 32 can be used with any configuration of distal ends 16 and 38.

Figure 12:
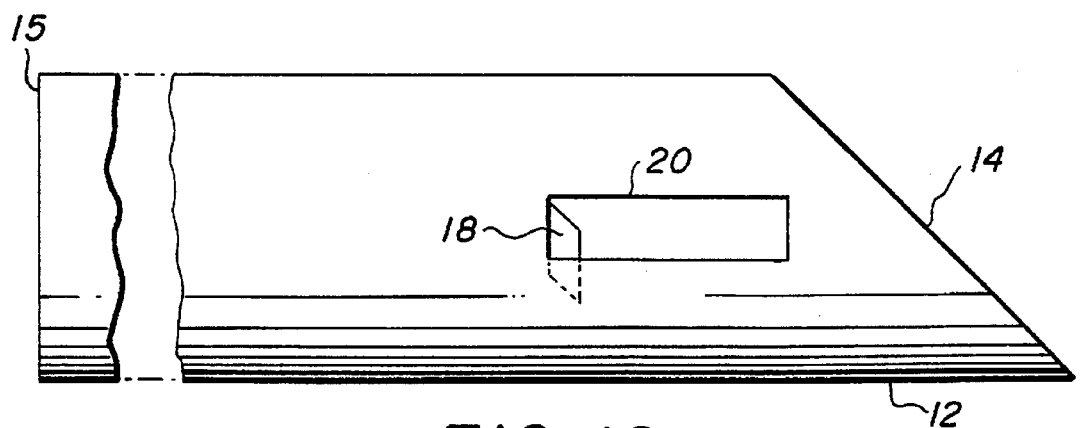
FIG. 12 is a side view of the needle showing a second alternative embodiment of the invention for use as an arterial needle.
Figure 13:
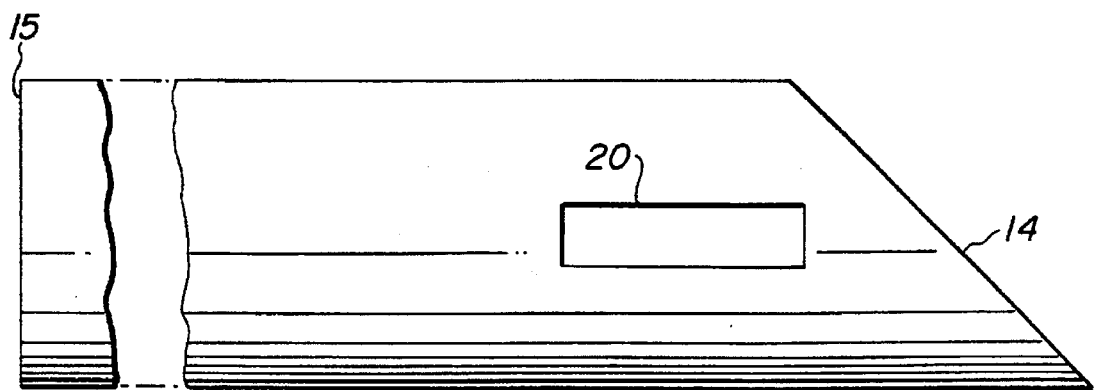
FIG. 13 is a side view of the needle showing an alternative embodiment of the second alternative embodiment of the invention for use as an arterial needle.

In a second alternative embodiment of the invention, as shown in FIGS. 12 and 13, the needle 10 may be used as an arterial rather than as a venous needle with minor modifications. In this embodiment, diverters 18 may be located between lateral openings 20 and proximal opening 15. It will be obvious to one of ordinary skill in the art that all the alternative embodiments discussed above will also apply when the diverters 18 are differently situated. Thus, this redundant description will not be included. In an alternative embodiment to the second alternative embodiment, the needle may be used without diverters as shown in FIG. 13.

The instant invention has been shown and described herein in what is considered to be the most practical and preferred embodiment. It is recognized, however, that departures may be made therefrom within the scope of the invention and that obvious modifications will occur to a person skilled in the art.

I claim:

1. A dialysis needle comprising:
   a hollow shaft having an exterior surface, an interior surface, a central axis, an open proximal end, an open distal end, and at least two lateral openings; and
   at least two non-pivotable diverters located on said interior surface of said hollow shaft, each of said diverters positioned adjacent an associated one of said lateral openings, each of said diverters being fixed in position and projecting into a lumen of said hollow shaft at an angle toward said central axis of said hollow shaft.

2. The dialysis needle according to claim 1, wherein said lateral openings are evenly spaced around a circumference of said hollow shaft.

3. The dialysis needle according to claim 1, wherein each of said diverters is located between said associated one of said lateral openings and said distal end.

4. The dialysis needle according to claim 1, wherein each of said diverters is located between said associated one of said lateral openings and said proximal end.

5. The dialysis needle according to claim 1, wherein said distal end is bevelled.

6. The dialysis needle according to claim 1, wherein each of said diverters projects at least 0.1 mm into said hollow shaft.

7. A dialysis needle comprising:
   a hollow shaft having an exterior surface, an interior surface, a central axis, an open proximal end, an open distal end, and at least two lateral openings;
   at least two non-pivotable diverters located on said interior surface of said hollow shaft, each of said diverters adjacent an associated one of said lateral openings, each of said diverters projecting into a lumen of said hollow shaft at an angle toward said central axis of said hollow shaft; and
   a trocar having a shaft and a distal end, said trocar being disposed within said hollow shaft.

8. A dialysis needle according to claim 7, wherein said distal end of said trocar is bevelled and said distal end of said hollow shaft is blunt.

9. A dialysis needle according to claim 7, wherein said distal end of said trocar is blunt and said distal end of said hollow shaft is bevelled.

10. A dialysis needle comprising:

a hollow shaft having an exterior surface, an interior surface, a central axis, an open proximal end, an open distal end, and at least one lateral opening, said lateral opening located between 0.8 mm and 2.0 mm from said distal end; and a non-pivotable diverter located on said interior surface of said hollow shaft adjacent said lateral opening, said diverter projecting into a lumen of said hollow shaft at an angle toward said central axis of said hollow shaft.

11. A dialysis needle comprising:

a hollow shaft having an exterior surface, an interior surface, a central axis, an open proximal end, an open distal end, and at least one lateral opening, said lateral opening located between 0.8 mm and 2.0 mm from said distal end;

a non-pivotable diverter located on said interior surface of said hollow shaft adjacent said lateral opening, said diverter projecting into a lumen of said hollow shaft at an angle toward said central axis of said hollow shaft; and a trocar having a shaft and a distal end, said trocar being disposed within said hollow shaft.

\* \* \* \* \*